(12) United States Patent
Almansa Rosales et al.

(10) Patent No.: US 8,476,456 B2
(45) Date of Patent: Jul. 2, 2013

(54) PROCESS FOR THE PREPARATION OF 4-(IMIDAZOL-1-YL) BENZENESULFONAMIDE DERIVATIVES

(75) Inventors: Carmen Almansa Rosales, Barcelona (ES); Concepción González González, Cornellà (ES)

(73) Assignee: Palau Pharma, S.A., Palau-solita i Plegamans (ES)

( * ) Notice: Subject to any disclaimer, the term of this patent is extended or adjusted under 35 U.S.C. 154(b) by 934 days.

(21) Appl. No.: 12/060,574

(22) Filed: Apr. 1, 2008

(65) Prior Publication Data

US 2009/0012307 A1  Jan. 8, 2009

Related U.S. Application Data

(62) Division of application No. 10/485,950, filed as application No. PCT/ES02/00385 on Aug. 1, 2002, now Pat. No. 7,351,836.

(30) Foreign Application Priority Data

Aug. 7, 2001 (ES) .................................. 200101853

(51) Int. Cl.
C07D 233/68  (2006.01)
(52) U.S. Cl.
USPC ....................................................... 548/343.1
(58) Field of Classification Search
USPC ....................................................... 548/343.1
See application file for complete search history.

(56) References Cited

U.S. PATENT DOCUMENTS 6,743,816 B2 *  6/2004  Almansa Rosales et al. .. 514/397
6,838,476 B1 *  1/2005  Almansa et al. ............... 514/399

FOREIGN PATENT DOCUMENTS

WO  WO 99/64415 A1  12/1999
WO  WO 00/23426 A1  4/2000
WO  WO 01/70704 A1  9/2001

OTHER PUBLICATIONS

Johnson et al., CA 6:22088, 1912.

* cited by examiner

Primary Examiner — Laura L. Stockton
(74) Attorney, Agent, or Firm — Rothwell, Figg, Ernst & Manbeck P.C.

(57) ABSTRACT

Process for the preparation of 4-(imidazol-1-yl)benzenesulfonamide derivatives of formula I, wherein $R^1$ represents optionally substituted aryl or heteroaryl, which comprises treating a compound of formula II, wherein $R^1$ has the same meaning defined in the formula I and $Bu^t$ represents tert-butyl, with an acid. The 4-(imidazol-1-yl)benzenesulfonamide derivatives of formula I are useful as anti-inflammatory agents.

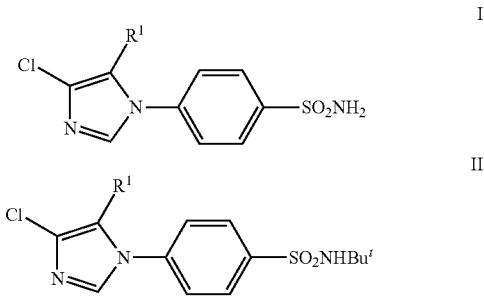

15 Claims, No Drawings

PROCESS FOR THE PREPARATION OF 4-(IMIDAZOL-1-YL) BENZENESULFONAMIDE DERIVATIVES

This application is a Divisional of U.S. Ser. No. 10/485,950, filed Jul. 27, 2004, now U.S. Pat. No. 7,351,836, which was a 371 filing of PCT/ES02/00385, filed Aug. 1, 2002 which claims priority from Spanish PO101853, filed Aug. 7, 2001. All prior applications are incorporated herein by reference.

FIELD OF THE INVENTION

The present invention relates to a new process for the preparation of 4-(imidazol-1-yl)benzenesulfonamide derivatives, which are useful in therapy.

DESCRIPTION OF THE PRIOR ART

Patent application WO 00/23426 discloses a series of imidazole derivatives with potent anti-inflammatory activity. A preferred subgroup of compounds in this patent are those imidazoles having a phenylsulfonamide substituent, which compounds can be depicted by means of the formula I:

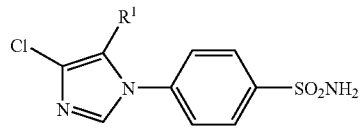

wherein:

$R^1$ represents aryl or heteroaryl optionally substituted with one or more groups independently selected from halogen, $C_{1-8}$ alkyl, $C_{1-8}$ haloalkyl, $R^2OC_{0-8}$ alkyl, $R^2SC_{0-8}$ alkyl, cyano, nitro, —$NR^2R^4$, —$NR^2SO_2R^3$, —$SOR^3$, —$SO_2R^3$, —$SO_2NR^2R^4$ or —$CONR^2R^4$;

$R^2$ represents hydrogen, $C_{1-8}$ alkyl or aryl$C_{0-8}$ alkyl (wherein the aryl group can be optionally substituted with one or more groups selected from $C_{1-8}$ alkyl, halogen, $C_{1-8}$ haloalkyl, cyano, nitro, $R^5OC_{0-8}$ alkyl, $R^5SC_{0-8}$ alkyl, —$NR^5R^6$, —$NR^5COR^3$, —$COR^5$ or —$COOR^5$);

$R^3$ represents $C_{1-8}$ alkyl or $C_{1-8}$ haloalkyl;

$R^4$ represents hydrogen, $C_{1-8}$ alkyl, aryl$C_{1-8}$ alkyl (wherein the aryl group can be optionally substituted with one or more groups selected from $C_{1-8}$ alkyl, halogen, $C_{1-8}$ haloalkyl, cyano, nitro, $R^5OC_{0-8}$ alkyl, $R^5SC_{0-8}$ alkyl, —$NR^5R^6$, —$NR^5COR^3$, —$COR^5$, or —$COOR^5$), —$COR^6$ or —$COOR^6$;

$R^5$ represents hydrogen, $C_{1-8}$ alkyl or benzyl;

$R^6$ represents $C_{1-8}$ alkyl or $C_{1-8}$ haloalkyl;

aryl represents phenyl or naphthyl; and heteroaryl represents pyridine, pyrazine, pyrimidine or pyridazine, which can be optionally fused to a benzene ring.

Among the compounds of formula I, the compounds 4-[4-chloro-5-(3-fluoro-4-methoxyphenyl)imidazol-1-yl]benzenesulfonamide and 4-[4-chloro-5-(4-ethoxyphenyl)imidazol-1-yl]benzenesulfonamide are particularly preferred.

The method disclosed in WO 00/23426 to prepare these 4-(imidazol-1-yl)benzenesulfonamide derivatives of formula I involves the conversion of the corresponding methylsulfoxide derivative —$SOCH_3$ (i.e., a [4-(imidazol-1-yl)phenyl] methylsulfoxide) into the sulfonamide —$SO_2NH_2$ by a process which comprises treating said —$SOCH_3$ derivative with acetic anhydride to give the corresponding acetoxymethylthio derivative (—$SCH_2OAc$), which is then oxidized to give the corresponding —$SO_2CH_2OAc$ derivative, treatment of the latter with a base to give the corresponding sodium sulfinate —$SO_2Na$, and finally treatment of the —$SO_2Na$ derivative with hydroxylamino-O-sulfonic acid. This synthesis has a high number of steps, for which reason the global yield of the process for preparing the compounds of formula I is low. There is thus the need to find an alternative process to prepare the sulfonamide derivatives of formula I. This problem is solved by the process of the present invention, which has a lower number of steps than the process disclosed in the prior art, provides the compounds of formula I with higher yields and can be used on an industrial scale.

DESCRIPTION OF THE INVENTION

Thus, an aspect of the present invention relates to a new process for the preparation of a compound of formula I,

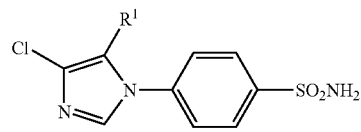

wherein:

$R^1$ represents aryl or heteroaryl optionally substituted with one or more groups independently selected from halogen, $C_{1-8}$ alkyl, $C_{1-8}$ haloalkyl, $R^2OC_{0-8}$ alkyl, $R^2SC_{0-8}$ alkyl, cyano, nitro, —$NR^2R^4$, —$NR^2SO_2R^3$, —$SOR^3$, —$SO_2R^3$, —$SO_2NR^2R^4$ or —$CONR^2R^4$;

$R^2$ represents hydrogen, $C_{1-8}$ alkyl or aryl$C_{0-8}$ alkyl (wherein the aryl group can be optionally substituted with one or more groups selected from $C_{1-8}$ alkyl, halogen, $C_{1-8}$ haloalkyl, cyano, nitro, $R^5OC_{0-8}$ alkyl, $R^5SC_{0-8}$ alkyl, —$NR^5R^6$, —$NR^5COR^3$, —$COR^5$ or —$COOR^5$);

$R^3$ represents $C_{1-8}$ alkyl or $C_{1-8}$ haloalkyl;

$R^4$ represents hydrogen, $C_{1-8}$ alkyl, aryl$C_{1-8}$ alkyl (wherein the aryl group can be optionally substituted with one or more groups selected from $C_{1-8}$ alkyl, halogen, $C_{1-8}$ haloalkyl, cyano, nitro, $R^5OC_{0-8}$ alkyl, $R^5SC_{0-8}$ alkyl, —$NR^5R^6$, —$NR^5COR^3$, —$COR^5$, or —$COOR^5$), —$COR^6$ or —$COOR^6$;

$R^5$ represents hydrogen, $C_{1-8}$ alkyl or benzyl;

$R^6$ represents $C_{1-8}$ alkyl or $C_{1-8}$ haloalkyl;

aryl represents phenyl or naphthyl; and heteroaryl represents pyridine, pyrazine, pyrimidine or pyridazine, which can be optionally fused to a benzene ring;

which comprises treating a compound of formula II

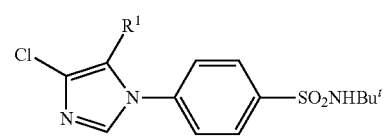

wherein $R^1$ has the meaning defined above in relation to the formula I and $Bu^t$ represents tert-butyl, with an acid.

Another aspect of the present invention relates to a process for the preparation of a compound of formula II

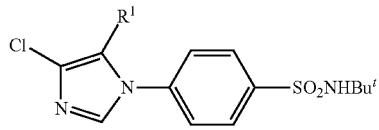

wherein $R^1$ has the meaning defined above in relation to the formula I and $Bu^t$ represents tert-butyl, which comprises reacting 4-amino-N-tert-butylbenzenesulfonamide of formula III

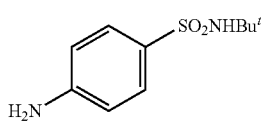

wherein $Bu^t$ represents tert-butyl, with an aldehyde of formula $R^1$—CHO (IV), wherein $R^1$ has the meaning defined above, to give an imine of formula V

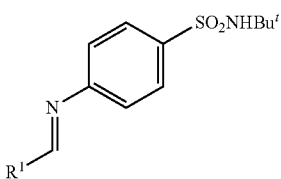

wherein $R^1$ and $Bu^t$ have the meaning defined above, then allowing to react said imine of formula V with a methylisocyanide of formula L-$CH_2$—NC (VI), wherein L represents a good leaving group, in the presence of a base, to give an imidazole derivative of formula VII

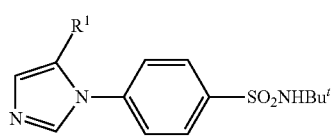

wherein $R^1$ and $Bu^t$ have the meaning defined above, and finally chlorinating said compound of formula VII by treatment with a chlorinating agent.

Another aspect of the present invention relates to a process for the preparation of a compound of formula I

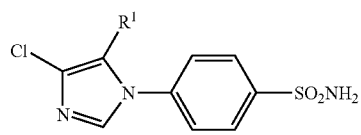

wherein $R^1$ has the meaning defined above, which comprises reacting 4-amino-N-tert-butylbenzenesulfonamide of formula III

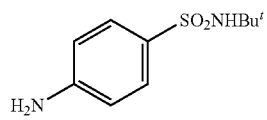

wherein $Bu^t$ represents tert-butyl, with an aldehyde of formula $R^1$—CHO (IV), wherein $R^1$ has the meaning defined above, to give an imine of formula V

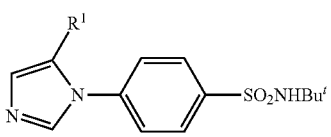

wherein $R^1$ and $Bu^t$ have the meaning defined above, next allowing to react said imine of formula V with a methylisocyanide of formula L-$CH_2$—NC (VI), wherein L represents a good leaving group, in the presence of a base, to give an imidazole derivative of formula VII

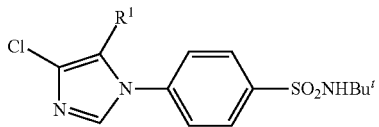

wherein $R^1$ and $Bu^t$ have the meaning defined above, then chlorinating said compound of formula VII by treatment with a chlorinating agent, to give a compound of formula II

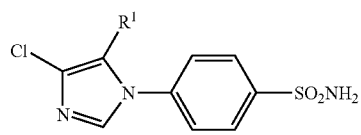

wherein $R^1$ and $Bu^t$ have the meaning defined above, and finally treating said compound of formula II with an acid.

The novel intermediates of formulae II, V and VII, useful to prepare the compounds of formula I, are another aspect of the present invention.

In the above definitions, the term $C_{1-8}$ alkyl, as a group or part of a group, means a linear or branched alkyl group having from 1 to 8 carbon atoms. Examples thereof include among others the groups methyl, ethyl, propyl, isopropyl, butyl, isobutyl, sec-butyl, tert-butyl, pentyl, isopentyl, neopentyl, hexyl, heptyl and octyl. A $C_{0-8}$ alkyl group means that additionally the alkyl group can be absent (i.e. a covalent bond is present).

A halogen group or its abbreviation halo means fluoro, chloro, bromo or iodo.

A C$_{1-8}$ haloalkyl group means a group resulting from the substitution of one or more hydrogen atoms of a C$_{1-8}$ alkyl group with one or more halogen atoms (i.e., fluoro, chloro, bromo or iodo), which can be the same or different. Examples include trifluoromethyl, fluoromethyl, 1-chloroethyl, 2-chloroethyl, 1-fluoroethyl, 2-fluoroethyl, 2-bromoethyl, 2-iodoethyl, pentafluoroethyl, 3-fluoropropyl, 3-chloropropyl, 2,2,3,3-tetrafluoropropyl, 2,2,3,3,3-pentafluoropropyl, heptafluoropropyl, 4-fluorobutyl, nonafluorobutyl, 5-fluoropentyl, 6-fluorohexyl, 7-fluoroheptyl and 8-fluorooctyl.

An arylC$_{1-8}$ alkyl group means a group resulting from the substitution of a hydrogen atom of a C$_{1-8}$ alkyl group with an aryl group such as those defined above, i.e. phenyl or naphthyl, which can be optionally substituted as indicated above. Examples thereof include among others the groups benzyl, 1-phenylethyl, 2-phenylethyl, 3-phenylpropyl, 2-phenylpropyl, 1-phenylpropyl, 4-phenylbutyl, 3-phenylbutyl, 2-phenylbutyl, 1-phenylbutyl, 5-phenylpentyl, 6-phenylhexyl, 7-phenylheptyl and 8-phenyloctyl, wherein the phenyl group can be optionally substituted. An arylC$_{0-8}$ alkyl group means that it additionally includes an aryl group when the alkyl group is absent (i.e., when it is C$_0$ alkyl).

As already mentioned above in each of the definitions where the term appears, the aryl or heteroaryl groups can be optionally substituted with one or more, preferably from one to three, groups selected in each case from a certain group of substituents. The substituent(s), when there is more than one, can be in any available position of the aryl or heteroaryl group.

In a preferred embodiment, in the processes disclosed above R$^1$ represents phenyl or pyridine optionally substituted with one or more groups independently selected from halogen, C$_{1-8}$ alkyl, C$_{1-8}$ haloalkyl, R$^2$OC$_{0-8}$ alkyl, R$^2$SC$_{0-8}$ alkyl, cyano, nitro, —NR$^2$R$^4$, —NR$^2$SO$_2$R$^3$, —SOR$^3$, —SO$_2$R$^3$, —SO$_2$NR$^2$R$^4$, or —CONR$^2$R$^4$.

In a more preferred embodiment, R$^1$ represents phenyl or pyridine optionally substituted with one or more groups independently selected from halogen, C$_{1-8}$ alkyl, C$_{1-8}$ haloalkyl, R$^2$OC$_{0-8}$ alkyl, R$^2$SC$_{0-8}$ alkyl, —NR$^2$R$^4$ or —SO$_2$R$^3$.

In a still more preferred embodiment, R$^1$ represents phenyl optionally substituted with one or more groups independently selected from halogen and R$^2$OC$_{0-8}$ alkyl.

In a particularly preferred embodiment, R$^1$ represents 3-fluoro-4-methoxyphenyl and the compound of formula I obtained is 4-[4-chloro-5-(3-fluoro-4-methoxyphenyl)imidazol-1-yl]benzenesulfonamide.

In another particularly preferred embodiment, R$^1$ represents 4-ethoxyphenyl and the compound of formula I obtained is 4-[4-chloro-5-(4-ethoxyphenyl)imidazol-1-yl]benzenesulfonamide.

As explained above, the compounds of formula I are obtained from the compounds of formula II by removal of the sulfonamide-protecting tert-butyl group, as shown in the following scheme:

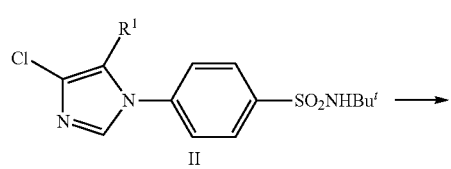

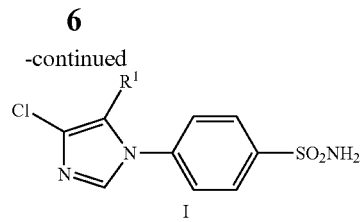

wherein R$^1$ has the meaning described above and Bu$^t$ represents tert-butyl.

The removal of the tert-butyl group from a compound of formula II is carried out by treatment with an acid. Examples of suitable acids to carry out said deprotection include trifluoroacetic acid, hydrochloric acid and phosphoric acid. The reaction can be carried out optionally in a solvent and at a temperature preferably comprised between room temperature and that of the boiling point of the solvent, in case such solvent is present. As preferred reaction conditions we can mention hydrochloric acid in aqueous medium at reflux, or trifluoroacetic acid, optionally in dichloromethane, at room temperature.

The compound of formula I thus obtained can be isolated by conventional methods and can be purified using standard procedures well known to those skilled in the art, such as for example by recrystallization from a suitable solvent such as for example acetonitrile, methanol, ethanol or isopropanol.

The compounds of formula II are prepared as shown in the following scheme:

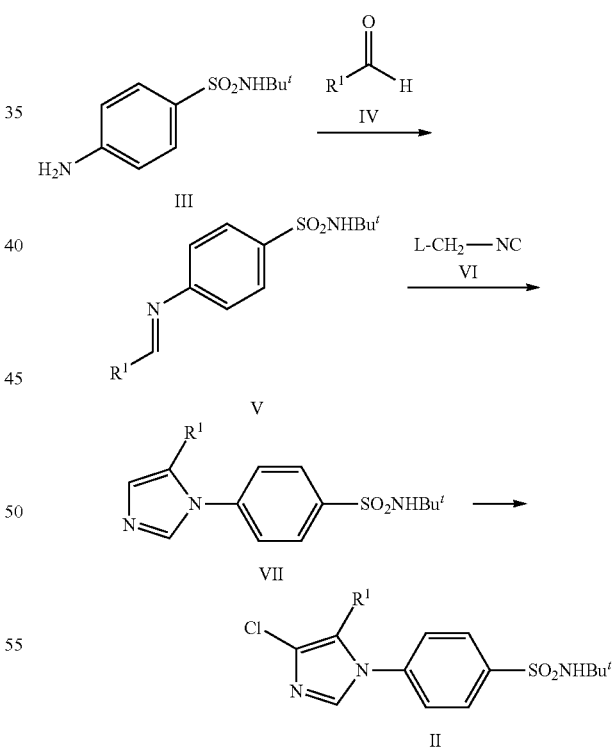

wherein R$^1$ has the meaning described above for the compounds of formula I, L represents a good leaving group and Bu$^t$ represents tert-butyl.

In a first step, 4-amino-N-tert-butylbenzenesulfonamide of formula III is allowed to react with an aldehyde of formula R$^1$—CHO (IV), wherein R$^1$ has the meaning described above, to give an imine of formula V. Said condensation is carried out by heating at reflux in a suitable solvent such as toluene or benzene and optionally in the presence of acid catalysis such as for example p-toluenesulfonic acid, in an azeotropic distillation system.

The imine obtained (V) is then reacted with a methylisocyanide of formula L-CH$_2$—NC (VI), wherein L is a good leaving group, in the presence of a base, in a suitable solvent and at a temperature comprised between room temperature and that of the boiling point of the solvent, to give an imidazole of formula VIII. Preferably, the reaction can be carried out using tosylmethylisocyanide as the compound of formula VI, a base such as K$_2$CO$_3$ and a solvent such as dimethylformamide or methanol-dimethoxyethane mixtures, and heating, preferably at reflux.

Finally, the imidazole obtained (VII) is chlorinated at the position 4 of the ring by treatment with a suitable chlorinating agent and in a suitable solvent, to give a compound of formula II. As preferred chlorinating agent we can mention N-chlorosuccinimide and as preferred solvent we can mention acetonitrile. The reaction is carried out by heating, preferably at reflux.

The starting product 4-amino-N-tert-butylbenzenesulfonamide (III) can be obtained for example by means of any of the two synthetic pathways depicted in the following scheme:

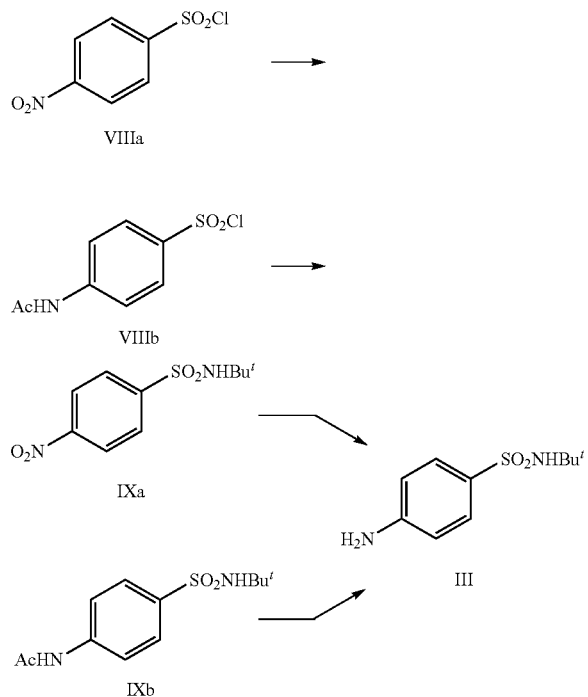

wherein Bu$^t$ represents tert-butyl and Ac represents acetyl.

Thus, 4-amino-N-tert-butylbenzenesulfonamide III can be prepared from a N-tert-butylbenzenesulfonamide of formula IXa or IXb. When starting from N-tert-butyl-4-nitrobenzenesulfonamide (IXa), the compound III is obtained by reduction of the nitro group using any of the methods widely described in the literature for the reduction of nitro groups. Thus, for example, suitable reducing agents are hydrogen in the presence of palladium on carbon and in a suitable solvent such as ethanol or methanol, or SnCl$_2$ in a suitable solvent such as for example ethanol. When starting from 4-acetylamino-N-tert-butylbenzenesulfonamide (IXb), compound III is obtained by deprotection of the amine, for example under basic conditions, using a base such as KOH in a suitable solvent, for example water or water-methanol mixtures. The N-tert-butylbenzenesulfonamides of formulae IXa and IXb can be obtained from the corresponding sulfonyl chloride (VIIIa and VIIIb, respectively) by reaction with tert-butylamine in a suitable solvent such as for example tetrahydrofuran, dimethoxyethane or ethyl acetate, at a temperature comprised between room temperature and that of the boiling point of the solvent.

The compounds of formulae VI, VIIIa and VIIIb are commercially available. The aldehydes of formula IV, depending upon their structure, are either commercially available or can be prepared using methods described in the literature, for example as described in WO 00/23426.

The invention is now illustrated with the following examples, which are not to be understood as limiting the scope of the present invention in any way.

The following abbreviations have been used in the examples:
THF: tetrahydrofuran
TMS: tetramethylsilane
EtOH: ethanol
DME: dimethoxyethane
Et$_2$O: diethyl ether
MeOH: methanol
EtOAc: ethyl acetate
Bu$^t$: tert-butyl
Ac: acetyl

EXAMPLE 1

4-Amino-N-tert-butylbenzenesulfonamide

Method A:

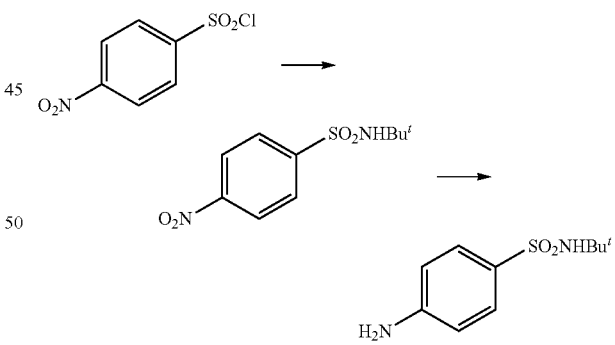

a) N-tert-Butyl-4-nitrobenzenesulfonamide

To a solution of tert-butylamine (0.47 L, 6.4 mol) in THF (0.55 L) is slowly added, at 0° C., a solution of 4-nitrobenzenesulfonyl chloride (50 g, 0.23 mol) in THF (0.55 L) and the resulting mixture is stirred for 24 h at room temperature. The solvent is removed and the residue is taken up in a CHCl$_3$/0.5 N HCl mixture, the layers are separated and the aqueous phase is extracted with CHCl$_3$. The combined organic extracts are washed with H$_2$O and brine and dried over MgSO$_4$. The solvent is removed, yielding 56.3 g of a yellowish solid which is directly used in the next reaction (yield: 97%).

Mp: 105-109° C.; $^1$H-NMR (300 MHz, CDCl$_3$) δ (TMS): 1.29 (s, 9H), 5.07 (s, 1H), 8.13 (d, J=9 Hz, 2H), 8.39 (d, J=9 Hz, 2H).

b) Title Compound

A solution of N-tert-butyl-4-nitrobenzenesulfonamide (10.0 g, 39 mmol) in EtOH (100 mL) is stirred for 48 h under a H$_2$ atmosphere in the presence of 10% Pd/C (1.50 g). The resulting mixture is filtered and concentrated to give the desired product as a slightly-coloured solid (8.7 g, yield: 98%).

Mp: 127° C.; $^1$H-NMR (300 MHz, CDCl$_3$+CD$_3$OD) δ (TMS): 1.19 (s, 9H), 3.74 (s, CD$_3$OD+1H), 6.93 (d, J=9 Hz, 2H), 7.66 (d, J=9 Hz, 2H).

Method B:

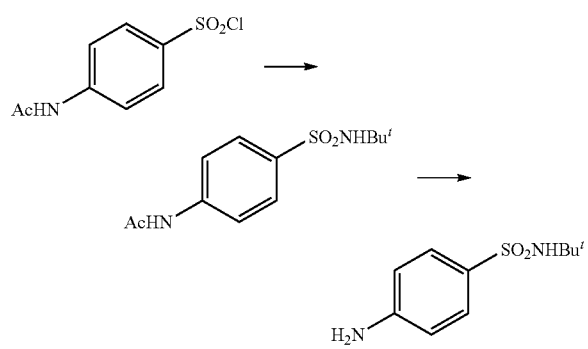

a) 4-Acetylamino-N-tert-butylbenzenesulfonamide

To a suspension of 4-acetylaminobenzenesulfonyl chloride (10 g, 43 mmol) in DME (103 mL) is added, at 0° C., tert-butylamine (9 mL, 86 mmol) in DME (103 mL). Next, the reaction mixture is stirred for 4 h at reflux. The solvent is removed and CHCl$_3$ is added. The resulting suspension is filtered and the solid is washed with CHCl$_3$, H$_2$O and Et$_2$O. The solid obtained is dried in vacuo to give 8.0 g of the product as a white solid (yield: 68%).

Mp: 200-201° C.; $^1$H-NMR (300 MHz, CDCl$_3$+CD$_3$OD) δ (TMS): 1.15 (s, 9H), 2.12 (s, 3H), 4.21 (s, 2H+CD$_3$OD), 7.66 (d, J=9 Hz, 2H), 7.75 (d, J=9 Hz, 2H).

b) Title Compound

A solution of 4-acetylamino-N-tert-butylbenzenesulfonamide (8.0 g, 29.6 mmol), KOH (8.30 g, 148 mmol), H$_2$O (6 mL) and MeOH (24 mL) is heated at 100° C. for 2 h. H$_2$O (24 mL) is added and the mixture is heated for two more hours. It is allowed to cool, H$_2$O is added and it is brought to pH 8 with 1N HCl. It is then extracted with EtOAc, dried over Na$_2$SO$_4$ and the solvent is removed, to give 6.0 g of the product as a white solid (yield: 89%).

EXAMPLE 2

N-tert-Butyl-4-[(3-fluoro-4-methoxybenzylidene)amino]benzenesulfonamide

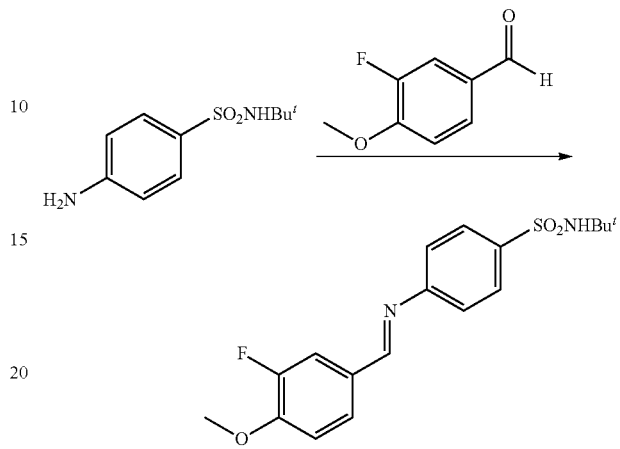

A mixture of 4-amino-N-tert-butylbenzenesulfonamide (52.3 g, 0.23 mol, obtained in example 1), 3-fluoro-4-methoxybenzaldehyde (35.3 g, 0.23 mol) and toluene (2.5 L) is heated at reflux in a Dean-Stark for 24 h. The solvent is removed, yielding 83.5 g of the title compound (yield: quantitative).

Mp: 129-131° C.; $^1$H-NMR (300 MHz, CDCl$_3$) δ (TMS): 1.23 (s, 9H), 3.98 (s, 3H), 4.65 (s, 1H), 7.04 (t, J=8.1 Hz, 1H), 7.21 (d, J=6.7 Hz, 2H), 7.58 (m, 1H), 7.73 (dd, J$_{H-F}$=11.8 Hz, J=2 Hz, 1H), 7.90 (d, J=6.7 Hz, 2H), 8.33 (s, 1H).

EXAMPLE 3

N-tert-Butyl-4-[5-(3-fluoro-4-methoxyphenyl)imidazol-1-yl]benzenesulfonamide

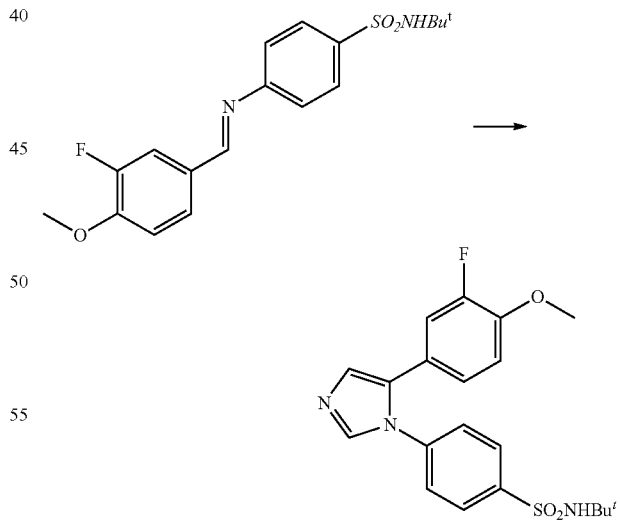

A mixture of N-tert-butyl-4-[(3-fluoro-4-methoxybenzylidene)amino]benzenesulfonamide (41.5 g, 114 mmol, obtained in example 2), tosylmethylisocyanide (33.22 g, 171 mmol), K$_2$CO$_3$ (31.1 g, 228 mmol), DME (340 mL) and MeOH (778 mL) is heated at reflux for 3 h. The solvent is removed and the residue is taken up in a CHCl$_3$/H$_2$O mixture and the layers are separated. The aqueous phase is extracted with CHCl$_3$ and the combined organic extracts are dried over MgSO$_4$ and concentrated. A crude product is obtained, which is washed with Et$_2$O several times to give 41.40 g of a creamy solid that is directly used in the next reaction (yield: 90%).

Mp: 229-232° C.; $^1$H-NMR (300 MHz, CDCl$_3$) δ (TMS): 1.24 (s, 9H), 3.89 (s, 3H), 4.51 (s, 1H), 6.90 (m, 3H), 7.23 (s, 1H), 7.29 (d, J=8.7 Hz, 2H), 7.73 (s, 1H), 7.94 (d, J=8.7 Hz, 2H).

EXAMPLE 4

N-tert-Butyl-4-[4-chloro-5-(3-fluoro-4-methoxyphenyl)imidazol-1-yl]benzenesulfonamide

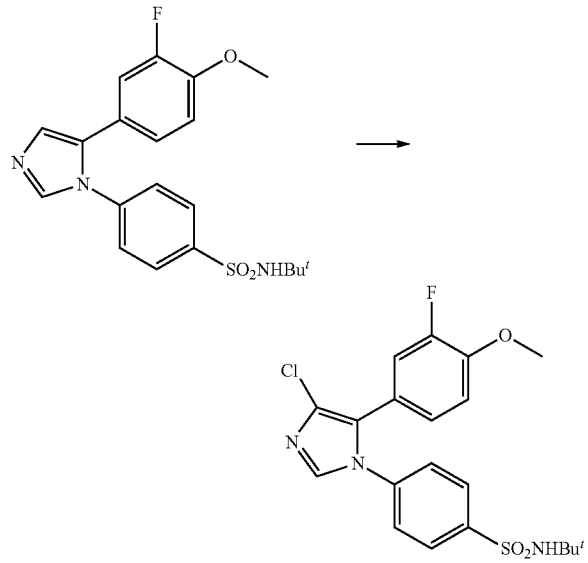

A mixture of N-tert-butyl-4-[5-(3-fluoro-4-methoxyphenyl)imidazol-1-yl]benzenesulfonamide (41.40 g, 103 mmol, obtained in example 3) and acetonitrile (840 mL) is heated at reflux and acetonitrile is added until complete dissolution (200 mL more). Next, N-chlorosuccinimide (15.0 g, 113 mmol) is added and the mixture is refluxed for 24 h. The solvent is removed and the residue is suspended in EtOAc and 1N HCl and is stirred for 10 min. The solid obtained is filtered and washed directly in the filter with 1N HCl, 1N NaOH, saturated NH$_4$Cl solution, H$_2$O and Et$_2$O. A solid is obtained, which is dried in vacuo to give 37.0 g of the product as a creamy solid (yield: 82%).

Mp: 208-210° C.; $^1$H-NMR (300 MHz, CDCl$_3$) δ (TMS): 1.24 (s, 9H), 3.89 (s, 3H), 4.51 (s, 1H), 6.90 (m, 3H), 7.23 (d, J=8.7 Hz, 2H), 7.63 (s, 1H), 7.92 (d, J=8.7 Hz, 2H).

EXAMPLE 5

4-[4-Chloro-5-(3-fluoro-4-methoxyphenyl)imidazol-1-yl]benzenesulfonamide

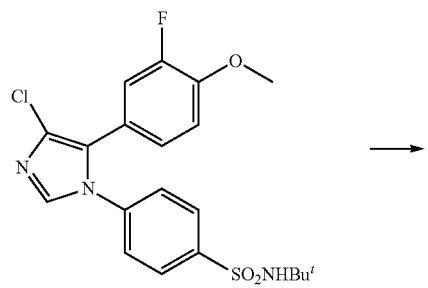

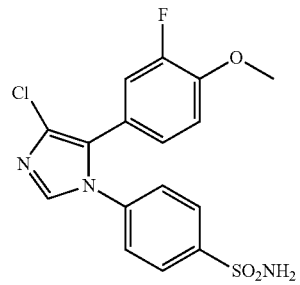

A mixture of N-tert-butyl-4-[4-chloro-5-(3-fluoro-4-methoxyphenyl)imidazol-1-yl]benzenesulfonamide (37.0 g, 85 mmol, obtained in example 4), concentrated HCl (200 mL) and H$_2$O (200 mL) is heated at reflux for 3 h. The mixture is allowed to cool and is brought to pH 6 with 6N NaOH. A white precipitate appears, which is collected by filtration and washed with plenty of H$_2$O and then with CHCl$_3$. 31 g of the title compound of the example is obtained (yield: 97%), which are recrystallized from acetonitrile.

Mp: 211-212° C.; $^1$H-NMR (300 MHz, CDCl$_3$+CD$_3$OD) δ (TMS): 3.90 (s, 3H), 4.16 (s, CD$_3$OD+2H), 6.93 (m, 3H), 7.30 (d, J=8.6 Hz, 2H), 7.73 (s, 1H), 7.95 (d, J=8.7 Hz, 2H).

EXAMPLE 6

N-tert-Butyl-4-[(4-ethoxybenzylidene)amino]benzenesulfonamide

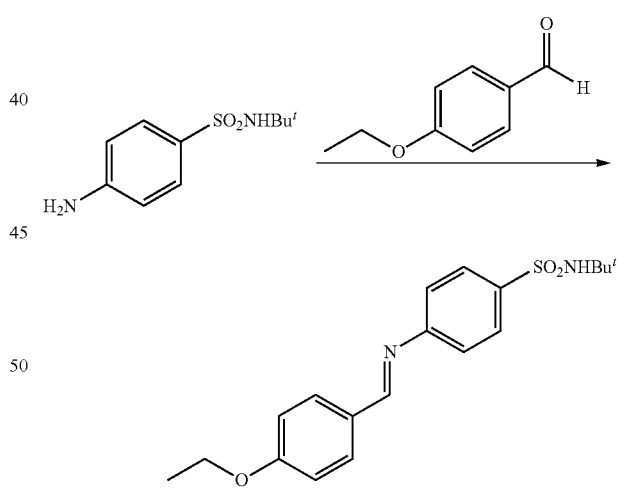

Following a similar process to that described in example 2, but using 4-ethoxybenzaldehyde instead of 3-fluoro-4-methoxybenzaldehyde, the title compound is obtained in quantitative yield.

Mp: 188° C.; $^1$H-NMR (300 MHz, CDCl$_3$+CD$_3$OD) δ (TMS): 1.23 (s, 9H), 1.46 (t, J=7.0 Hz, 3H), 3.83 (s, CD$_3$OD+1H), 4.13 (q, J=7.0 Hz, 2H), 7.00 (d, J=8.8 Hz, 2H), 7.25 (d, J=8.6 Hz, 2H), 7.85 (d, J=8.8 Hz, 2H), 7.89 (d, J=8.6 Hz, 2H), 8.38 (s, 1H).

EXAMPLE 7

N-tert-Butyl-4-[5-(4-ethoxyphenyl)imidazol-1-yl]benzenesulfonamide

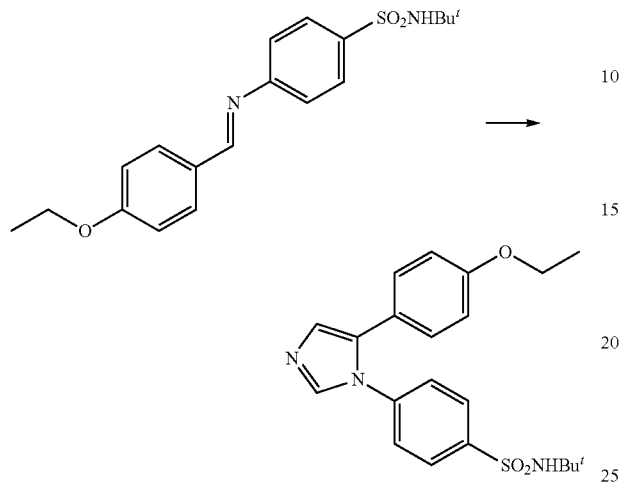

Following a similar process to that described in example 3, but starting from N-tert-butyl-4-[(4-ethoxybenzylidene)amino]benzenesulfonamide (obtained in example 6) instead of from N-tert-butyl-4-[(3-fluoro-4-methoxybenzylidene)amino]benzenesulfonamide, the title compound is obtained in 77% yield.

Mp: 215° C.; $^1$H-NMR (300 MHz, CDCl$_3$) δ (TMS): 1.25 (s, 9H), 1.41 (t, J=7.0 Hz, 3H), 4.01 (q, J=7.0 Hz, 2H), 4.59 (s, 1H), 6.79 (d, J=8.8 Hz, 2H), 7.01 (d, J=8.8 Hz, 2H), 7.20 (s, 1H), 7.28 (d, J=8.6 Hz, 2H), 7.72 (s, 1H), 7.91 (d, J=8.6 Hz, 2H).

EXAMPLE 8

N-tert-Butyl-4-[4-chloro-5-(4-ethoxyphenyl)imidazol-1-yl]benzenesulfonamide

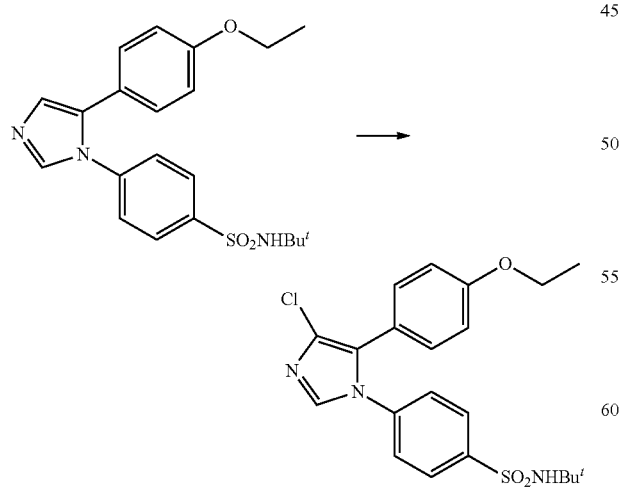

Following a similar process to that described in example 4, but starting from N-tert-butyl-4-[5-(4-ethoxyphenyl)imidazol-1-yl]benzenesulfonamide (obtained in example 7) instead of from N-tert-butyl-4-[5-(3-fluoro-4-methoxyphenyl)imidazol-1-yl]benzenesulfonamide, the title compound is obtained in 81% yield.

Mp: 189° C.; $^1$H-NMR (300 MHz, CDCl$_3$) δ (TMS): 1.24 (s, 9H), 1.42 (t, J=7.0 Hz, 3H), 4.02 (q, J=7.0 Hz, 2H), 4.49 (s, 1H), 6.82 (d, J=8.7 Hz, 2H), 7.08 (d, J=8.7 Hz, 2H), 7.22 (d, J=8.6 Hz, 2H), 7.63 (s, 1H), 7.89 (d, J=8.6 Hz, 2H)

EXAMPLE 9

4-[4-Chloro-5-(4-ethoxyphenyl)imidazol-1-yl]benzenesulfonamide

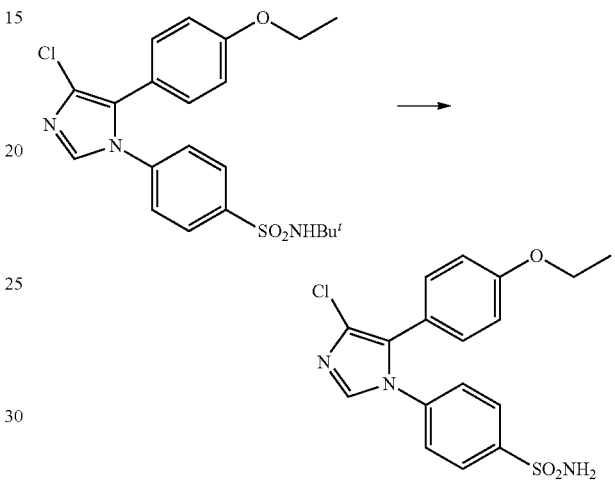

Method A

Following a similar process to that described in example 5, but starting from N-tert-butyl-4-[4-chloro-5-(4-ethoxyphenyl)imidazol-1-yl]benzenesulfonamide (obtained in example 8) instead of from N-tert-butyl-4-[4-chloro-5-(3-fluoro-4-methoxyphenyl)imidazol-1-yl]benzenesulfonamide, the title compound is obtained in 89% yield.

Mp: 265-267° C.; $^1$H-NMR (300 MHz, CDCl$_3$+CD$_3$OD) δ (TMS): 1.42 (t, J=7.0 Hz, 3H), 4.03 (q, J=7.0 Hz, 2H), 4.08 (s, 2H), 6.86 (d, J=8.6 Hz, 2H), 7.11 (d, J=8.6 Hz, 2H), 7.28 (d, J=8.5 Hz, 2H), 7.70 (s, 1H), 7.94 (d, J=8.5 Hz, 2H).

Method B

A mixture of N-tert-butyl-4-[4-chloro-5-(4-ethoxyphenyl)imidazol-1-yl]benzenesulfonamide (0.25 g, 0.565 mmol, obtained in example 8) and trifluoroacetic acid (3 mL) is stirred at room temperature overnight. The resulting mixture is concentrated and partitioned between CHCl$_3$ and H$_2$O. Then it is made basic with 1N NaOH and the layers are separated. The organic phase is extracted with 0.1N NaOH and once the layers are separated, the aqueous phase is brought to pH 5 with 1N HCl. The solid formed is filtered and washed with H$_2$O to give 173 mg of the title compound (yield: 81%).

The invention claimed is:
1. A compound of formula II

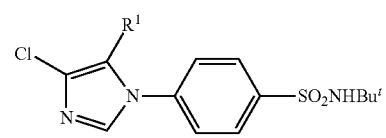

II wherein:
R¹ represents 3-fluoro-4-methoxyphenyl or 4-ethoxyphenyl and $Bu^t$ represents tert-butyl.

2. A process for the preparation of a compound of formula II

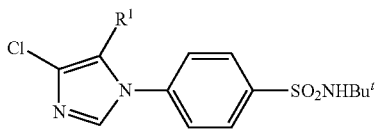

wherein R¹ represents aryl or heteroaryl optionally substituted with one or more groups independently selected from halogen, $C_{1-8}$ alkyl, $C_{1-8}$ haloalkyl, $R^2OC_{0-8}$ alkyl, $R^2SC_{0-8}$ alkyl, cyano, nitro, —$NR^2R^4$, —$NR^2SO_2R^3$, —$SOR^3$, —$SO_2R^3$, —$SO_2NR^2R^4$ or —$CONR^2R^4$;

R² represents hydrogen, $C_{1-8}$ alkyl or $arylC_{0-8}$ alkyl (wherein the aryl group can be optionally substituted with one or more groups selected from $C_{1-8}$ alkyl, halogen, $C_{1-8}$ haloalkyl, cyano, nitro, $R^5OC_{0-8}$ alkyl, $R^5SC_{0-8}$ alkyl, —$NR^5R^6$, —$NR^5COR^3$, —$COR^5$ or —$COOR^5$);

R³ represents $C_{1-8}$ alkyl or $C_{1-8}$ haloalkyl;

R⁴ represents hydrogen, $C_{1-8}$ alkyl, $arylC_{1-8}$ alkyl (wherein the aryl group can be optionally substituted with one or more groups selected from $C_{1-8}$ alkyl, halogen, $C_{1-8}$ haloalkyl, cyano, nitro, $R^5OC_{0-8}$ alkyl, $R^5SC_{0-8}$ alkyl, —$NR^5R^6$, —$NR^5COR^3$, —$COR^5$, or —$COOR^5$), —$COR^6$ or —$COOR^6$;

R⁵ represents hydrogen, $C_{1-8}$ alkyl or benzyl;

R⁶ represents $C_{1-8}$ alkyl or $C_{1-8}$ haloalkyl;

aryl represents phenyl or naphthyl; and heteroaryl represents pyridine, pyrazine, pyrimidine or pyridazine, which can be optionally fused to a benzene ring;

and $Bu^t$ represents tert-butyl, which comprises reacting 4-amino-N-tert-butylbenzenesulfonamide of formula III

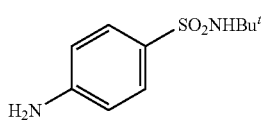

wherein $Bu^t$ represents tert-butyl, with an aldehyde of formula R¹—CHO (IV), wherein R¹ has the meaning defined above, to produce an imine of formula V

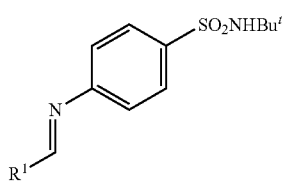

wherein R¹ and $Bu^t$ have the meaning defined above, then allowing to react said imine of formula V with a methylisocyanide of formula L-$CH_2$—NC (VI), wherein L represents a leaving group, in the presence of a base, to produce an imidazole derivative of formula VII

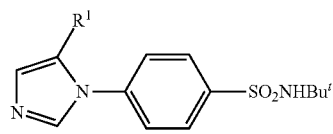

wherein R¹ and $Bu^t$ have the meaning defined above, and chlorinating said compound of formula VII by treatment with a chlorinating agent to produce a compound of formula II.

3. A process according to claim 2 wherein R¹ represents phenyl or pyridine optionally substituted with one or more groups independently selected from halogen, $C_{1-8}$ alkyl, $C_{1-8}$ haloalkyl, $R^2OC_{0-8}$ alkyl, $R^2SC_{0-8}$ alkyl, cyano, nitro, —$NR^2R^4$, —$NR^2SO_2R^3$, —$SOR^3$, —$SO_2R^3$, —$SO_2NR^2R^4$, or —$CONR^2R^4$.

4. A process according to claim 2 wherein R¹ represents phenyl or pyridine optionally substituted with one or more groups independently selected from halogen, $C_{1-8}$ alkyl, $C_{1-8}$ haloalkyl, $R^2OC_{0-8}$ alkyl, $R^2SC_{0-8}$ alkyl, —$NR^2R^4$ or —$SO_2R^3$.

5. A process according to claim 2 wherein R¹ represents phenyl optionally substituted with one or more groups independently selected from halogen and $R^2OC_{0-8}$ alkyl.

6. A process according to claim 2 wherein R¹ represents 3-fluoro-4-methoxyphenyl and the compound of formula II obtained is N-tert-butyl-4-[4-chloro-5-(3-fluoro-4-methoxyphenyl)imidazol-1-yl]benzenesulfonamide.

7. A process according to claim 2 wherein R¹ represents 4-ethoxyphenyl and the compound of formula II obtained is N-tert-butyl-4-[4-chloro-5-(4-ethoxyphenyl)imidazol-1-yl]benzenesulfonamide.

8. A process according to claim 2 wherein the reaction of III with IV is carried out in toluene or benzene at reflux and optionally in the presence of acid catalysis.

9. A process according to claim 8 wherein the reaction is carried out in the presence of acid catalysis.

10. A process according to claim 9 wherein as acid catalysis p-toluenesulfonic acid is used.

11. A process according to claim 2 wherein the methylisocyanide of formula VI is tosylmethylisocyanide.

12. A process according to claim 2 wherein the reaction of V with VI is carried out using $K_2CO_3$ as the base.

13. A process according to claim 2 wherein the reaction of V with VI is carried out in dimethylformamide or methanol-dimethoxyethane mixtures.

14. A process according to claim 2 wherein the chlorinating agent is N-chlorosuccinimide.

15. A process according to claim 2 wherein the chlorination is carried out in acetonitrile.

* * * * *